United States Patent
Ishitsuka

(10) Patent No.: US 11,064,973 B2
(45) Date of Patent: Jul. 20, 2021

(54) ULTRASOUND PROBE AND ULTRASOUND DIAGNOSIS APPARATUS

(71) Applicant: CANON MEDICAL SYSTEMS CORPORATION, Otawara (JP)

(72) Inventor: Masaaki Ishitsuka, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 236 days.

(21) Appl. No.: 16/027,898

(22) Filed: Jul. 5, 2018

(65) Prior Publication Data

US 2019/0008477 A1 Jan. 10, 2019

(30) Foreign Application Priority Data

Jul. 6, 2017 (JP) .............................. JP2017-133110

(51) Int. Cl.
*A61B 8/14* (2006.01)
*A61B 8/08* (2006.01)
*A61B 8/00* (2006.01)
*G01S 15/89* (2006.01)
*G01S 7/52* (2006.01)

(52) U.S. Cl.
CPC ............ *A61B 8/145* (2013.01); *A61B 8/4488* (2013.01); *A61B 8/488* (2013.01); *A61B 8/5207* (2013.01); *A61B 8/5269* (2013.01); *A61B 8/54* (2013.01); *A61B 8/56* (2013.01); *G01S 7/52038* (2013.01); *G01S 15/8915* (2013.01); *G01S 15/8927* (2013.01); *G01S 15/8963* (2013.01)

(58) Field of Classification Search
CPC .................................................. G01S 15/8963
See application file for complete search history.

(56) References Cited

U.S. PATENT DOCUMENTS

| 2003/0176792 | A1* | 9/2003 | Kawagishi | G01S 15/8963 600/458 |
| 2005/0131299 | A1* | 6/2005 | Robinson | G01S 15/8963 600/447 |
| 2014/0155751 | A1 | 6/2014 | Banjanin et al. | |

FOREIGN PATENT DOCUMENTS

JP 2014-113490 6/2014

* cited by examiner

*Primary Examiner* — Katherine L Fernandez
*Assistant Examiner* — Colin T. Sakamoto
(74) *Attorney, Agent, or Firm* — Oblon, McClelland, Maier & Neustadt, L.L.P.

(57) ABSTRACT

An ultrasound probe according to an embodiment includes: transducer elements, phase reversal processing circuitry, and delay processing circuitry. The transducer elements, each of which is configured to generate a first echo signal by receiving a reflected wave of a first ultrasound wave and to generate a second echo signal by receiving a reflected wave of a second ultrasound wave corresponding to an ultrasound wave obtained by reversing the phase of the first ultrasound wave. The phase reversal processing circuitry is configured to reverse the phase of the second echo signal. The delay processing circuitry is configured to delay the first echo signal and the phase-reversed second echo signal.

9 Claims, 10 Drawing Sheets

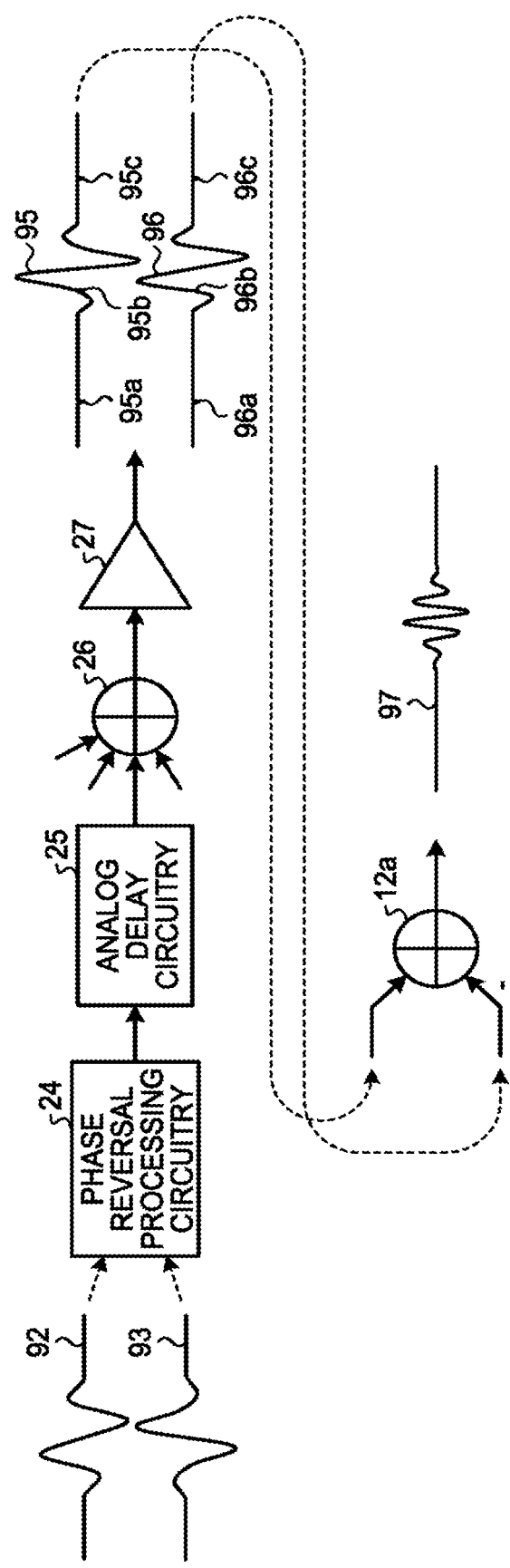

ULTRASOUND PROBE AND ULTRASOUND DIAGNOSIS APPARATUS

CROSS-REFERENCE TO RELATED APPLICATIONS

This application is based upon and claims the benefit of priority from Japanese Patent Application No. 2017-133110, filed on Jul. 6, 2017; the entire contents of which are incorporated herein by reference.

FIELD

Embodiments described herein relate generally to an ultrasound probe and an ultrasound diagnosis apparatus.

BACKGROUND

A known ultrasound diagnosis apparatus is configured to generate an ultrasound image in which an internal state of an examined subject (hereinafter, "patient") is expressed in a picture, by using an ultrasound probe that includes analog delay circuitry configured to perform a delay process on echo signals in an analog format.

Figure 9:
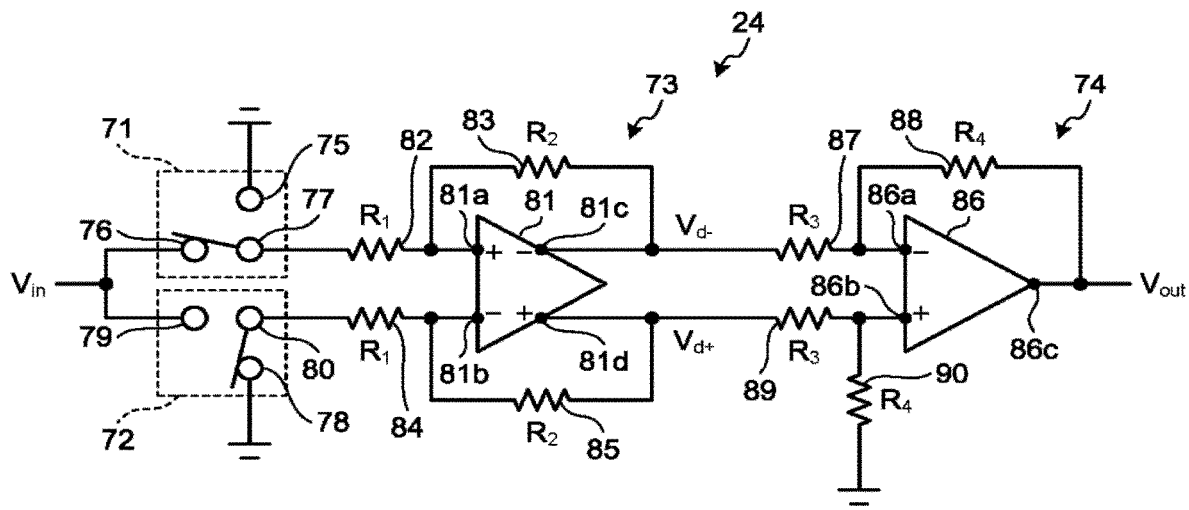
Figure 10:
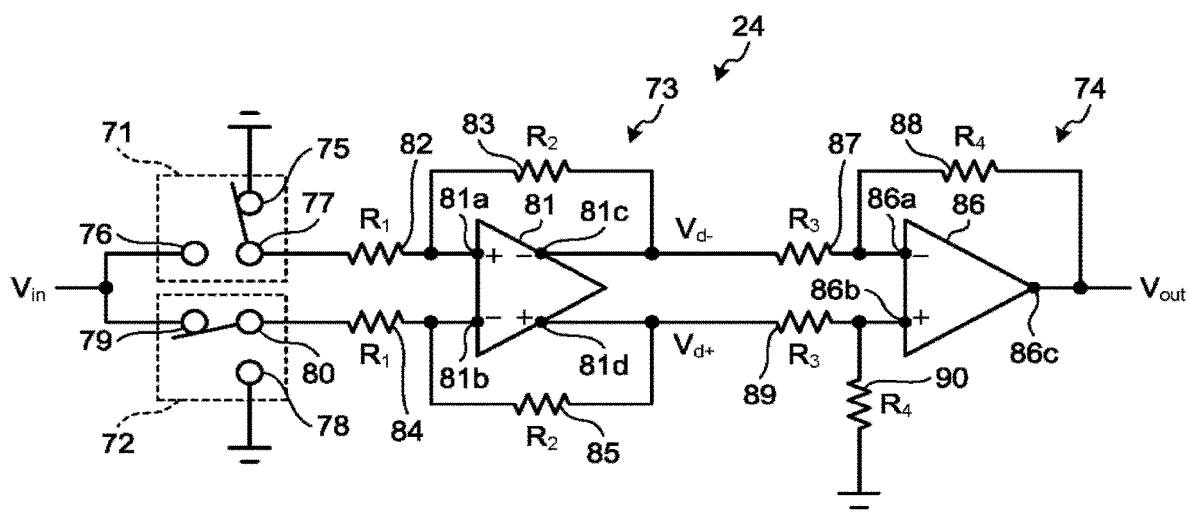
Figure 11:
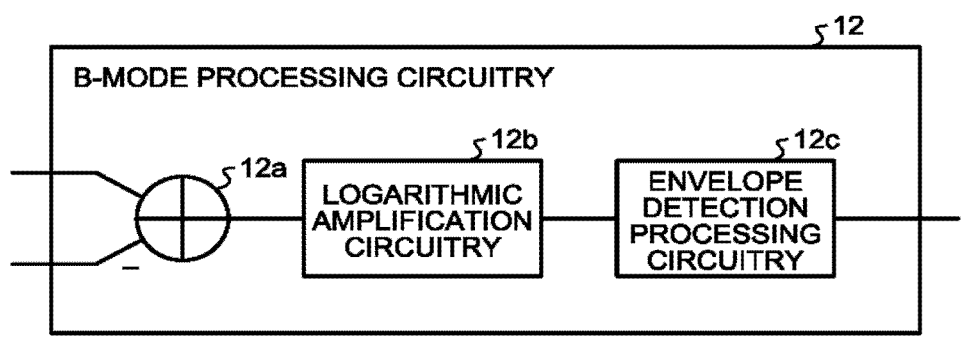

FIG. B is a chart for explaining an example of a process performed to reduce noise components caused by periodicity;

FIG. 9 is a diagram illustrating an exemplary configuration of phase reversal processing circuitry according to the embodiment;

FIG. 10 is a chart for explaining an example in which a second echo signal is input to the phase reversal processing circuitry;

FIG. 11 is a diagram illustrating an exemplary configuration of B-mode processing circuitry; and FIG. 12 is a diagram for explaining an example of a flow of various types of processes performed by the ultrasound diagnosis apparatus according to the embodiment.

DETAILED DESCRIPTION

An ultrasound probe according to an embodiment includes one or more transducer elements, phase reversal processing circuitry, and delay processing circuitry. The one or more transducer elements are configured to generate a first echo signal by receiving a reflected wave of a first ultrasound wave and to generate a second echo signal by receiving a reflected wave of a second ultrasound wave corresponding to an ultrasound wave obtained by reversing the phase of the first ultrasound wave. The phase reversal processing circuitry is configured to reverse the phase of the second echo signal. The delay processing circuitry is configured to delay the first echo signal and the phase-reversed second echo signal.

Exemplary embodiments of an ultrasound probe and an ultrasound diagnosis apparatus will be explained in detail below, with reference to the accompanying drawings.

Embodiments

Figure 1:
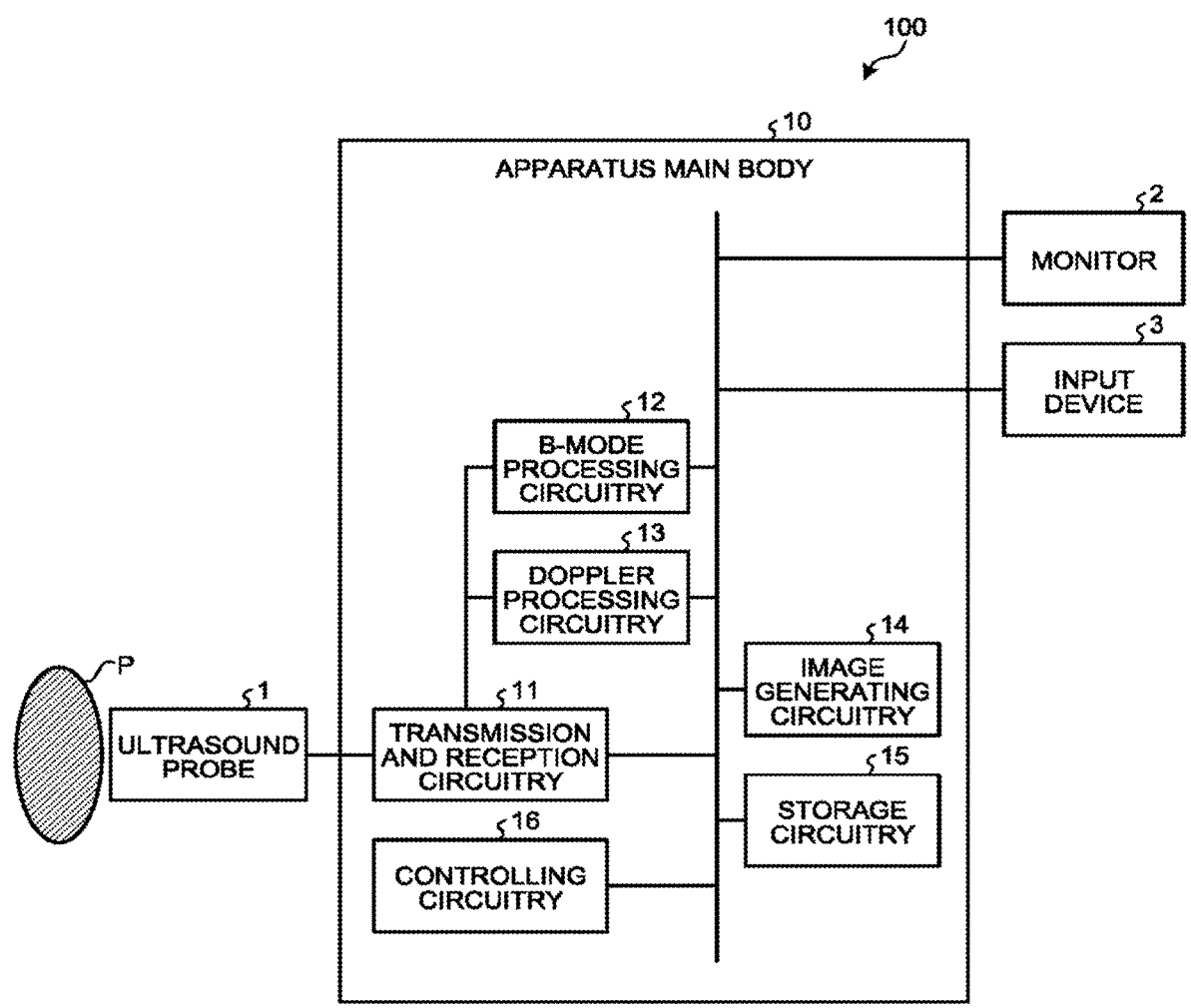
FIG. 1 is a diagram for explaining an exemplary configuration of an ultrasound diagnosis apparatus according to an embodiment.

First, an exemplary configuration of an ultrasound diagnosis apparatus to which an ultrasound probe according to an embodiment is applied will be explained. FIG. 1 is a diagram for explaining an exemplary configuration of an ultrasound diagnosis apparatus 100 according to the embodiment. As illustrated in FIG. 1, the ultrasound diagnosis apparatus 100 according to the embodiment includes an ultrasound probe 1, a monitor 2, an input device 3, and an apparatus main body 10.

The ultrasound probe 1 is detachably connected to the apparatus main body 10. When an ultrasound wave is transmitted from the ultrasound probe 1 to a patient P, the transmitted ultrasound wave is repeatedly reflected on a surface of discontinuity of acoustic impedances at a tissue in the body of the patient P. The reflected ultrasound wave is then received as an echo (a reflected wave) by the ultrasound probe 1. The echo is converted into an echo signal in the ultrasound probe 1. The amplitude of the echo signal is dependent on the difference between the acoustic impedances on the surface of discontinuity on which the ultrasound wave is reflected. When a transmitted ultrasound pulse is reflected on the surface of a moving blood flow, a cardiac wall, or like, the echo signal is, due to the Doppler effect, subject to a frequency shift, depending on a velocity component of the moving members with respect to the ultrasound wave transmission direction. When the ultrasound probe 1 is a two-dimensional array probe in which the transducer elements are two-dimensionally arranged, the echo signals is added in units of a certain number of channels in the ultrasound probe 1 and then output. In this way, the signal output from the ultrasound probe 1 is called an addition signal. The following describes a case where the ultrasound probe 1 is such a two-dimensional array probe. The ultrasound probe 1 may be of a convex type or a sector type. Any of various types of ultrasound probes can be used as the ultrasound probe 1.

The ultrasound probe 1 includes a plurality of transducer elements 21 (see FIG. 2) (explained later). The plurality of transducer elements 21 are two-dimensionally arranged along a lateral direction and an elevation direction and are divided into a plurality of sub-arrays. Each of the sub-arrays represents, for example, the positional arrangement of transducer elements 21 belonging to a different one of the groups that are formed by dividing the plurality of transducer elements 21 into the groups each having a predetermined number of transducer elements 21. Each of the sub-arrays is structured by the predetermined number of transducer elements 21. In the following sections, an example will be explained in which each of the sub-arrays is structured with four transducer elements 21; however, the number of transducer elements 21 structuring each of the sub-arrays is not limited to the one in the present example. For instance, each of the sub-arrays may be structured with 16 or 25 transducer elements 21. A configuration of the ultrasound probe 1 will be explained later.

The monitor 2 is configured to display a Graphical User Interface (GUI) used by a user of the ultrasound diagnosis apparatus 100 for inputting various types of setting requests through the input device 3 and to display an ultrasound image generated by the apparatus main body 10 and the like.

The input device 3 is realized with a trackball, a switch, a dial, a touch command screen, a foot switch, a joystick, and/or the like. The input device 3 is configured to receive the various types of setting requests from the user of the ultrasound diagnosis apparatus 100 and to transfer the received various types of setting requests the apparatus main body 10. For example, the input device 3 is configured to receive various types of setting requests to control the ultrasound probe 1 and to transfer the received requests to the apparatus main body 10.

The apparatus main body 10 is configured to control the transmission of the ultrasound waves by the ultrasound probe 1 and the reception of the echo by the ultrasound probe 1. Further, the apparatus main body 10 is configured to generate the ultrasound image on the basis of the addition signal transmitted thereto from the ultrasound probe 1. As illustrated in FIG. 1, the apparatus main body 10 includes transmission and reception circuitry 11, B-mode processing circuitry 12, Doppler processing circuitry 13, image generating circuitry 14, storage circuitry 15, and controlling circuitry 16.

The transmission and reception circuitry 11 is configured to transmit and receive various types of data between the ultrasound probe 1 and the apparatus main body 10, under control of the controlling circuitry 16. For example, the transmission and reception circuitry 11 is configured to transmit, to the ultrasound probe 1, a value of the amplitude of a drive signal transmitted by any of pieces of transmission circuitry 23 (explained later).

Further, the transmission and reception circuitry 11 is configured to transmit, to the ultrasound probe 1, a delay amount to be applied to each of the ultrasound waves transmitted from the ultrasound probe 1. In a specific example, the transmission and reception circuitry 11 is configured to transmit a delay amount to be applied to each of the ultrasound waves output (transmitted) by the transducer elements 21.

Further, the transmission and reception circuitry 11 is configured to transmit a delay amount to be applied to an echo signal. In a specific example, the transmission and reception circuitry 11 is configured to transmit a delay amount to be applied to each of the echo signals transmitted by the transducer elements 21.

Further, the transmission and reception circuitry 11 includes an analog-to-digital (A/D) converter and a reception beam former. When the transmission and reception circuitry 11 has received the addition signal in an analog format corresponding to any of the sub-arrays and having been output from the ultrasound probe 1, the A/D converter at first converts the addition signal in the analog format into an addition signal in a digital format. The reception beam former is configured to generate echo data by performing phased addition process on addition signals in the digital format corresponding to the sub-arrays. After that, the reception beam former is configured to transmit the generated echo data to the B-mode processing circuitry 12 and the Doppler processing circuitry 13.

The B-mode processing circuitry 12 is configured to receive the echo data output from the transmission and reception circuitry 11. Further, the B-mode processing circuitry 12 is configured to generate data (B-mode data) in which signal intensities are expressed by degrees of brightness, by performing a logarithmic amplification process, an envelope detection process, and/or the like on the received echo data. The B-mode processing circuitry 12 may be realized with a processor, for example.

Further, the B-mode processing circuitry 12 is configured to perform a signal processing process to realize a harmonic imaging process that expresses high-frequency components in a picture. Examples of the harmonic imaging process include a Tissue Harmonic Imaging (THI) process. A configuration of the B-mode processing circuitry 12 will be explained later.

The Doppler processing circuitry 13 is configured to receive the echo data output from the transmission and reception circuitry 11. Further, the Doppler processing circuitry 13 is configured to generate data (Doppler data) obtained by extracting moving member information such as average velocity, dispersion, power, and the like with respect to multiple points, by performing a frequency analysis to obtain velocity information from the received echo data and extracting blood flows, tissues, contrast agent echo components based on the Doppler effect. The Doppler processing circuitry 13 may be realized with a processor, for example.

The image generating circuitry 14 is configured to generate ultrasound images from the data generated by the B-mode processing circuitry 12 and the Doppler processing circuitry 13. In other words, the image generating circuitry 14 is configured to generate a B-mode image in which intensities of the echo are expressed with degrees of brightness, from the B-mode data generated by the B-mode processing circuitry 12. Further, the image generating circuitry 14 is configured to generate an average velocity image, a dispersion image, a power image, or a color Doppler image combining these types of images each of which expresses the moving member information, from the Doppler data generated by the Doppler processing circuitry 13. The image generating circuitry 14 may be realized with a processor, for example.

The storage circuitry 15 may be realized, for example, with a semiconductor memory element such as a Random Access Memory (RAM), a flash memory, or the like, or a hard disk, an optical disk, or the like. For example, the storage circuitry 15 is configured to store therein any of the ultrasound images generated by the image generating circuitry 14. Further, the storage circuitry 15 may store therein any of the data generated by the B-mode processing circuitry 12 and the Doppler processing circuitry 13.

Further, the storage circuitry 15 is configured to store therein control computer programs (hereinafter, "control programs") for performing ultrasound wave transmissions and receptions, image processing processes, and display processes as well as various types of data such as diagnosis information (e.g., patient's IDs, medical doctors' observations), diagnosis protocols, various types of body marks, and the like.

The controlling circuitry 16 is configured to control overall processes performed by the ultrasound diagnosis apparatus 100. For example, the controlling circuitry 16 is configured to control processes performed by the transmission and reception circuitry 11, the B-mode processing circuitry 12, the Doppler processing circuitry 13, and the image generating circuitry 14 on the basis of the various types of setting requests input by an operator via the input device 3 and any of the various types of control programs and the various types of data read from the storage circuitry 15. Further, the controlling circuitry 16 is configured to control the monitor 2 so as to display any of the ultrasound images stored in the storage circuitry 15, any of the various types of images stored in the storage circuitry 15, a GUI used for implementing processes performed by the image generating circuitry 14, processing results obtained by the image generating circuitry 14, or the like.

For example, the controlling circuitry 16 is configured to control the transmission and reception circuitry 11 so as to transmit the value of the amplitude of the drive signal to the ultrasound probe 1. Further, the controlling circuitry 16 is configured to control the transmission and reception circuitry 11 so as to transmit the delay amount to be applied to any of the ultrasound waves transmitted from the ultrasound probe 1, to the ultrasound probe 1. Further, the controlling circuitry 16 is configured to control the transmission and reception circuitry 11 so as to transmit the delay amount to be applied to any of the echo signals, to the ultrasound probe 1. For example, the controlling circuitry 16 may be realized with a processor.

The term "processor" used in the explanation above denotes, for example, a Central Processing Unit (CPU), a Graphics Processing Unit (GPU), or circuitry such as an Application Specific integrated Circuit (ASIC) or a programmable logic device (e.g., a Simple Programmable Logic Device [SPLD], a Complex Programmable Logic Device [CPLD], or a Field Programmable Gate Array [FPGA]). One or more processors realize the functions by reading the programs stored in the storage circuitry 15 and executing the read programs. Further, instead of saving the programs in the storage circuitry 15, it is also acceptable to directly incorporate the programs in the circuitry of the processors. In that situation, the processors realize the functions by reading the programs incorporated in the circuitry thereof and executing the read programs. Each of the processors according to the present embodiment does not necessarily have to be structured as a single piece of circuitry. It is acceptable to structure one processor by combining together a plurality of pieces of independent circuitry, so as to realize the functions thereof.

Figure 2:
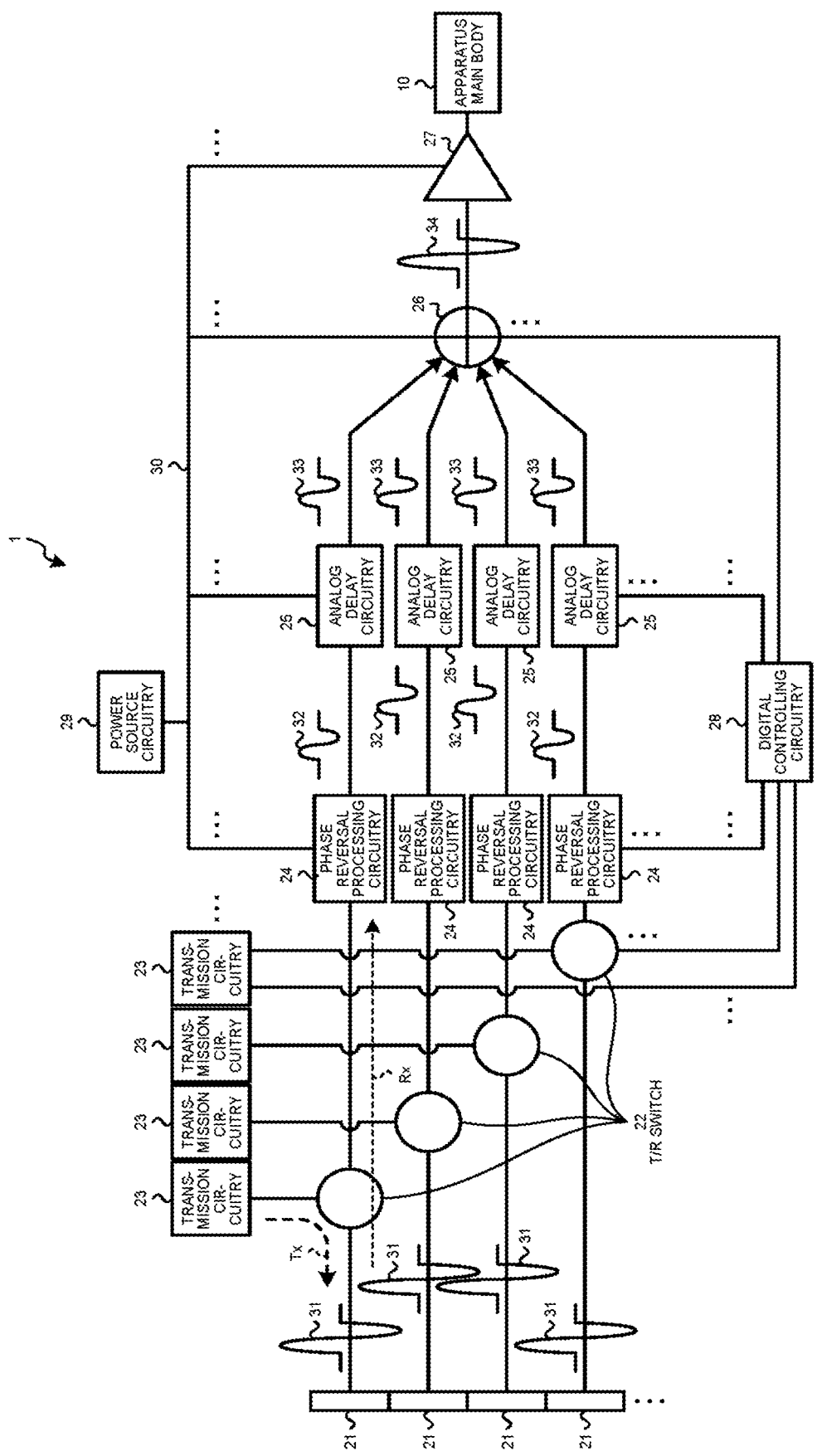
FIG. 2 is a diagram for explaining an exemplary configuration of an ultrasound probe according to the embodiment.

Next, an exemplary configuration of the ultrasound probe 1 according to the present embodiment will be explained, with reference to FIG. 2. FIG. 2 is a diagram for explaining the exemplary configuration of the ultrasound probe 1 according to the embodiment. FIG. 2 illustrates an exemplary configuration corresponding to one sub-array. Configurations corresponding to the other sub-arrays are omitted from the drawing.

As illustrated in FIG. 2, the ultrasound probe 1 includes the transducer elements 21, Transmission/Reception (T/R) switches 22, the transmission circuitry 23, phase reversal processing circuitry 24, analog delay circuitry 25, adding circuitry (an adder) 26, an output buffer 27, digital controlling circuitry 28, power source circuitry 29, and wiring 30.

In the present embodiment, the ultrasound probe 1 includes, with respect to the one sub-array, four transmission/reception switches 22, four pieces of transmission circuitry 23, four pieces of phase reversal processing circuitry 24, four pieces of analog delay circuitry 25, one piece of adding circuitry 26, one output buffer 27, one piece of power source circuitry 29, and one wiring 30. The ultrasound probe 1 includes as many sets as the total number of sub-arrays, each set being made up of these constituent elements corresponding to one sub-array.

In the present embodiment, one channel is assigned to each of the transducer elements 21. For each of the channels, a transmission/reception switch 22, a piece of transmission circuitry 23, a piece of phase reversal processing circuitry 24, and a piece of analog delay circuitry 25 are provided. In other words, for each of the transducer elements 21, a transmission/reception switch 22, a piece of transmission circuitry 23, a piece of phase reversal processing circuitry 24, and a piece of analog delay circuitry 25 are provided.

In contrast, a piece of adding circuitry 26, an output buffer 27, a piece of digital controlling circuitry 28, a piece of power source circuitry 29, and a wiring 30 are provided, not for each of the channels, but for each of the sub-arrays.

On the basis of a drive signal 31 supplied thereto from a corresponding one of the pieces of transmission circuitry 23, each of the transducer elements 21 is configured to transmit an ultrasound wave to the patient P. Further, when having received an echo of the ultrasound wave, each of the transducer elements 21 is configured to convert the received echo into an echo signal and to transmit the echo signal to a corresponding one of the transmission/reception switches 22.

Each of the transmission/reception switches 22 is configured to perform various types of switching operations under control of the digital controlling circuitry 28. For example, each of the transmission/reception switches 22 is configured to transmit the drive signal 31 transmitted thereto from the corresponding piece of transmission circuitry 23, to the corresponding transducer element 21. The arrow Tx schematically indicates the direction of the flow of the drive signal 31.

Further, each of the transmission/reception switches 22 is configured to transmit the echo signal transmitted thereto from the corresponding transducer element 21, to the corresponding piece of phase reversal processing circuitry 24. The arrow Rx indicates the direction of the flow of the echo signal.

The transmission circuitry 23 is configured to cause the ultrasound probe 1 to perform an ultrasound scan, under control of the digital controlling circuitry 28. For example, each of the pieces of transmission circuitry 23 generates the drive signal 31. Further, each of the pieces of transmission circuitry 2 performs a predetermined delay process on the generated drive signal 31. For example, under the control of the digital controlling circuitry 28, each of the pieces of transmission circuitry 23 is configured to perform a delay process of applying, to the drive signal 31, a delay amount that is required to converge the ultrasound wave generated from the corresponding transducer element 21 into the form of a beam and to determine transmission directionality. In this situation, the delay amount applied to the drive signal 31 is indicated by a control signal output from the digital controlling circuitry 28.

Further, each of the pieces of transmission circuitry 23 is configured to supply the corresponding transducer element 21 with the drive signal, by transmitting the drive signal 31 on which the prescribed delay process has been performed, to the corresponding transmission/reception switch 22. In this situation, each of the pieces of transmission circuitry 23 is configured to output, to the corresponding transducer element 21, the drive signal 31 of which the amplitude is adjusted to be equal to an amplitude value indicated by the control signal output from the digital controlling circuitry 28.

Further, when performing a tissue harmonic imaging process, the transmission circuitry 23 is configured to cause the ultrasound probe 1 to perform an ultrasound scan in which a set of ultrasound waves is transmitted, the set being made up of a first ultrasound wave and a second ultrasound wave corresponding to an ultrasound wave obtained by reversing the phase of the first ultrasound wave.

To explain a more specific example, after transmitting, to the corresponding transducer element 21, a drive signal that causes the first ultrasound wave to be transmitted, each of the pieces of transmission circuitry 23 transmits a drive signal that causes the second ultrasound wave to be transmitted, to the corresponding transducer element 21. As a result, the transducer element 21 generates a first echo signal by receiving an echo of the first ultrasound wave. Further, the transducer element 21 generates a second echo signal by receiving an echo of the second ultrasound wave.

When performing a tissue harmonic imaging process, each of the pieces of phase reversal processing circuitry 24 is configured to reverse the phase of the second echo signal, as being selected from between the first echo signal and the second echo signal. Further, each of the pieces of phase reversal processing circuitry 24 is configured to amplify the amplitude of the first echo signal and the phase-reversed second echo signal. In other words, each of the pieces of phase reversal processing circuitry 24 is configured to amplify the first echo signal and the second echo signal. After that, each of the pieces of phase reversal processing circuitry 24 is configured to transmit the amplified first echo signal and the amplified second echo signal to the corresponding piece of analog delay circuitry 25.

When performing a normal ultrasound scan, each of the pieces of phase reversal processing circuitry 24 is configured to amplify a corresponding echo signal 32 without reversing the phase of the echo signal 32 and to transmit the amplified echo signal 32 to the corresponding piece of analog delay circuitry 25. A configuration of the phase reversal processing circuitry 24 will be explained later.

Each of the pieces of analog delay circuitry 25 is analog circuitry and is configured to perform, upon receiving an echo signal, a delay process of applying a delay amount that is required to determine reception directionality to the received echo signal. Examples of the echo signal on which the delay process is performed include the first echo signal and the second echo signal described above. Further, each of the pieces of analog delay circuitry 25 is configured to transmit the echo signal on which the delay process has been performed, to the adding circuitry 26. As a result, as illustrated in FIG. 2, a plurality of echo signals 33 are output from the plurality of pieces of analog delay circuitry 25 by using timing that is substantially temporally the same among the echo signals 33. In this situation, the delay amount applied to each of the echo signals is a delay amount indicated by a control signal output from the digital controlling circuitry 28. The analog delay circuitry 25 is an example of the delay processing circuitry.

The adding circuitry 26 is configured to perform an adding process of adding together the plurality of echo signals 33 that were output from the plurality of transducer elements 21 (e.g., the four transducer elements 21 in the present embodiment) structuring the sub-array corresponding to the adding circuitry 26 and were delayed. Further, the adding circuitry 26 is configured to output one signal (an addition signal) 34 obtained as a result of the adding process, to the apparatus main body 10 via the output buffer 27. As a result of the adding process performed by the adding circuitry 26 while using the echo signals 33, reflection components from the directions corresponding to the reception directionality of the echo signals are emphasized. Because this adding process is performed for the channels in the sub-array, the adding function realized by the adding process within the ultrasound probe 1 may be referred to as a sub-array beam former.

For example, when performing a tissue harmonic imaging process, the adding circuitry 26 is configured to generate (create) a first addition signal by adding together a plurality of delayed first echo signals. Further, the adding circuitry 26 is configured to generate a second addition signal, by adding together a plurality of phase-reversed and delayed second echo signals. After that, the adding circuitry 26 is configured to output the first addition signal and the second addition signal via the output buffer 27. In this situation, the plurality of first echo signals and the plurality of second echo signals correspond to the plurality of (four) transducer elements 21.

The digital controlling circuitry 28 is configured to control operations of the transmission/reception switches 22, the transmission circuitry 23, the phase reversal processing circuitry 24, the analog delay circuitry 25, the adding circuitry 26, and the output buffer 27. The digital controlling circuitry 28 is an example of the controlling unit. In the following sections, the transmission/reception switches 22, the transmission circuitry 23, the phase reversal processing circuitry 24, the analog delay circuitry 25, the adding circuitry 26, and the output buffer 27 may collectively be referred to as controlled circuitry.

The digital controlling circuitry 26 is configured to control the controlled circuitry by transmitting various types of control signals to the controlled circuitry.

For example, the digital controlling circuitry 28 includes a register. When having received, from the controlling circuitry 16 via the transmission and reception circuitry 11, amplitude values of the drive signals to be transmitted by the pieces of transmission circuitry 23, the digital controlling circuitry 28 stores the received amplitude values of the drive signals to be transmitted by the pieces of transmission circuitry 23, into the register.

Further, when having received, from the controlling circuitry 16 via the transmit and reception circuitry 11, delay amounts to be applied the ultrasound waves to be transmitted by the transducer elements 21, the digital controlling circuitry 28 stores the received delay amounts to be applied to the ultrasound waves transmitted by the transducer elements 21, into the register.

Further, when having received, from the controlling circuitry 16 via the transmission and reception circuitry 11, delay amounts to be applied to the echo signals transmitted by the transducer elements 21, the digital controlling circuitry 28 stores the received delay amounts to be applied to the echo signals transmitted by the transducer elements 21, into the register.

After that, the digital controlling circuitry 28 obtains the amplitude values, which are stored in the register, of the drive signals to be output by the pieces of transmission circuitry 23. After that, the digital controlling circuitry 28 outputs the control signals each indicating the corresponding amplitude value, to the pieces of transmission circuitry 23. Accordingly, each of the pieces of transmission circuitry 23 either amplifies or attenuates the corresponding drive signal so as to have the amplitude indicated by the control signal output from the digital controlling circuitry 28 and thus outputs the amplitude-adjusted drive signal to the corresponding transducer element 1.

Further, the digital controlling circuitry 28 obtains the delay amounts, which are stored in the register, to be applied to the ultrasound waves transmitted by the transducer elements 21. After that, the digital controlling circuitry 28 outputs the control signals each indicating the delay amount to be applied to the corresponding ultrasound wave, to the pieces of transmission circuitry 23 corresponding to the transducer elements 21. Accordingly, each of the pieces of transmission circuitry 23 performs the delay process of applying the corresponding delay amount indicated by the control signal output from the digital controlling circuitry 28 to the corresponding drive signal and thus outputs the drive signal on which the delay process has been performed, to the corresponding transducer element 21.

Further, the digital controlling circuitry 28 obtains the delay amounts, which are stored in the register, to be applied to the echo signals transmitted by the transducer elements 21. After that, the digital controlling circuitry 28 outputs control signals each indicating the delay amount to be applied to the corresponding echo signal, to the pieces of analog delay circuitry 25 corresponding to the transducer elements 21. Accordingly, each of the pieces of analog delay circuitry 25 performs the delay process of applying the corresponding delay amount indicated by the control signal output from the digital controlling circuitry 28 to the echo signal output from the corresponding piece of phase reversal processing circuitry 24 and thus outputs the echo signal on which the delay process has been performed, to the adding circuitry 26.

The wiring 30 is configured to transfer the electric power supplied from the power source circuitry 29. The wiring 30 connects together the power source circuitry 29, the phase reversal processing circuitry 24, the analog delay circuitry 25, the adding circuitry 26, and the output buffer 27.

The power source circuitry is configured to supply, via the wiring 30, the electric power to the phase reversal processing circuitry 24, the analog delay circuitry 25, the adding circuitry 26, and the output buffer 27. For example, the power source circuitry 29 supplies the electric power by applying, via the wiring 30, voltage that operates the phase reversal processing circuitry 24, the analog delay circuitry 25, the adding circuitry 26, and the output buffer 27, to the phase reversal processing circuitry 24, the analog delay circuitry 25, the adding circuitry 26, and the output buffer 27.

Figure 3:
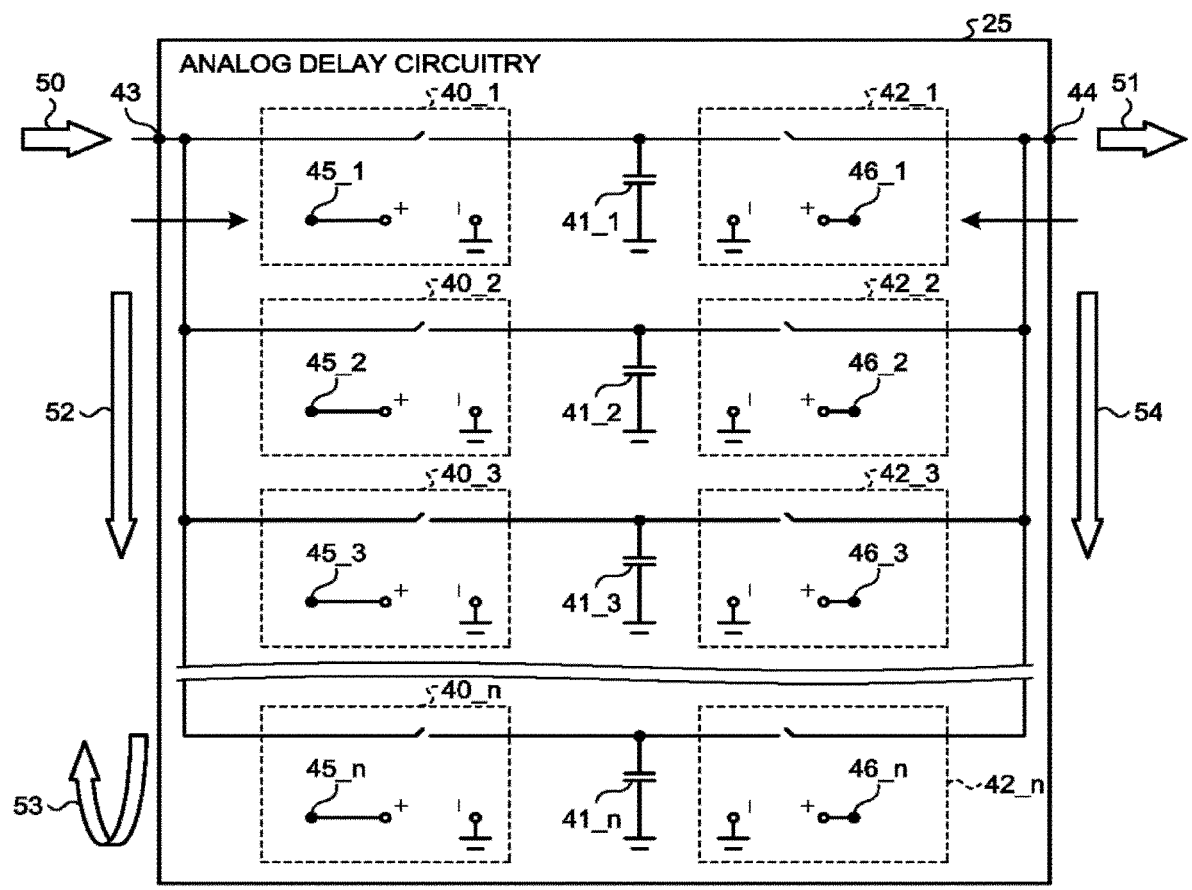
FIG. 3 is a diagram for explaining an exemplary configuration of analog delay circuitry according to the embodiment.

Next, an exemplary configuration of the analog delay circuitry 25 according to the embodiment will be explained, with reference to FIG. 3. FIG. 3 is a diagram for explaining the exemplary configuration of the analog delay circuitry 25 according to the embodiment.

The analog delay circuitry 25 illustrated in FIG. 3 is configured to sample echo signals by using a certain periodic cycle and to store therein echo signals each of which corresponds to a different one of the plurality of sampling points in time. Further, the analog delay circuitry 25 is configured to sequentially read the echo signals that were sampled and stored, by using timing corresponding to delay time periods and to transmit the read echo signals to the adding circuitry 26 as echo signals that are again successive.

As illustrated in FIG. 3, the analog delay circuitry includes: a plurality of write switches 40_1 to 40 (where n is a natural number of 2 or larger); a plurality of capacitors (condensers) 41_1 to 41_n serving as memory elements; a plurality of read switches 42_1 to 42_n; an echo signal input terminal 43; and an echo signal output terminal 44.

One end of the write switch 40_k (where k=1, 2, . . . n) is connected to the echo signal input terminal 43.

The echo signal input terminal 43 is connected to the corresponding piece of phase reversal processing circuitry 24. As schematically indicated by an arrow 50, to the echo signal input terminal 43, the echo signal from the corresponding piece of phase reversal processing circuitry 24 is input.

The other end of the write switch 40_k is connected to one end of the capacitor 41_k. The other end of the capacitor 41_k is earthed to a ground.

One end of the read switch 42_k is connected to one end of the capacitor 41_k. The other end of the read switch 42_k is connected to the echo signal output terminal 44.

The echo signal output terminal 44 is connected to the adding circuitry 26. As schematically indicated by an arrow 51, the delayed echo signal is output from the echo signal output terminal 44 to the adding circuitry 26.

Further, the write switch 40_k includes a control signal input terminal 45_k.

The control signal input terminal 45_k is connected to the digital controlling circuitry 20. To the control signal input terminal 45_k, a control signal for writing (a write control signal) is input from the digital controlling circuitry 28.

Each of the plurality of write switches 40_1 to 40_n is configured to sample an echo signal according to the corresponding write control signal and to write the echo signals at the sampling points in time to a corresponding one of capacitors 41_1 to 41_n. As a result, each of the plurality of capacitors 41_1 to 41_n stores therein the sampled echo signals.

Further, the read switch 42_k includes a control signal input terminal 46_n.

The control signal input terminal 46_k is connected to the digital controlling circuitry 28. To the control signal input terminal 46_k, a control signal for reading (a read control signal) is input from the digital controlling circuitry 28.

Each of the plurality of read switches 42_1 to 42_n is configured to read the echo signal sampled and written to stored into) the corresponding one of the plurality of capacitors 41_1 to 41_n according to the corresponding read control signal and to output the read echo signal.

Figure 4:
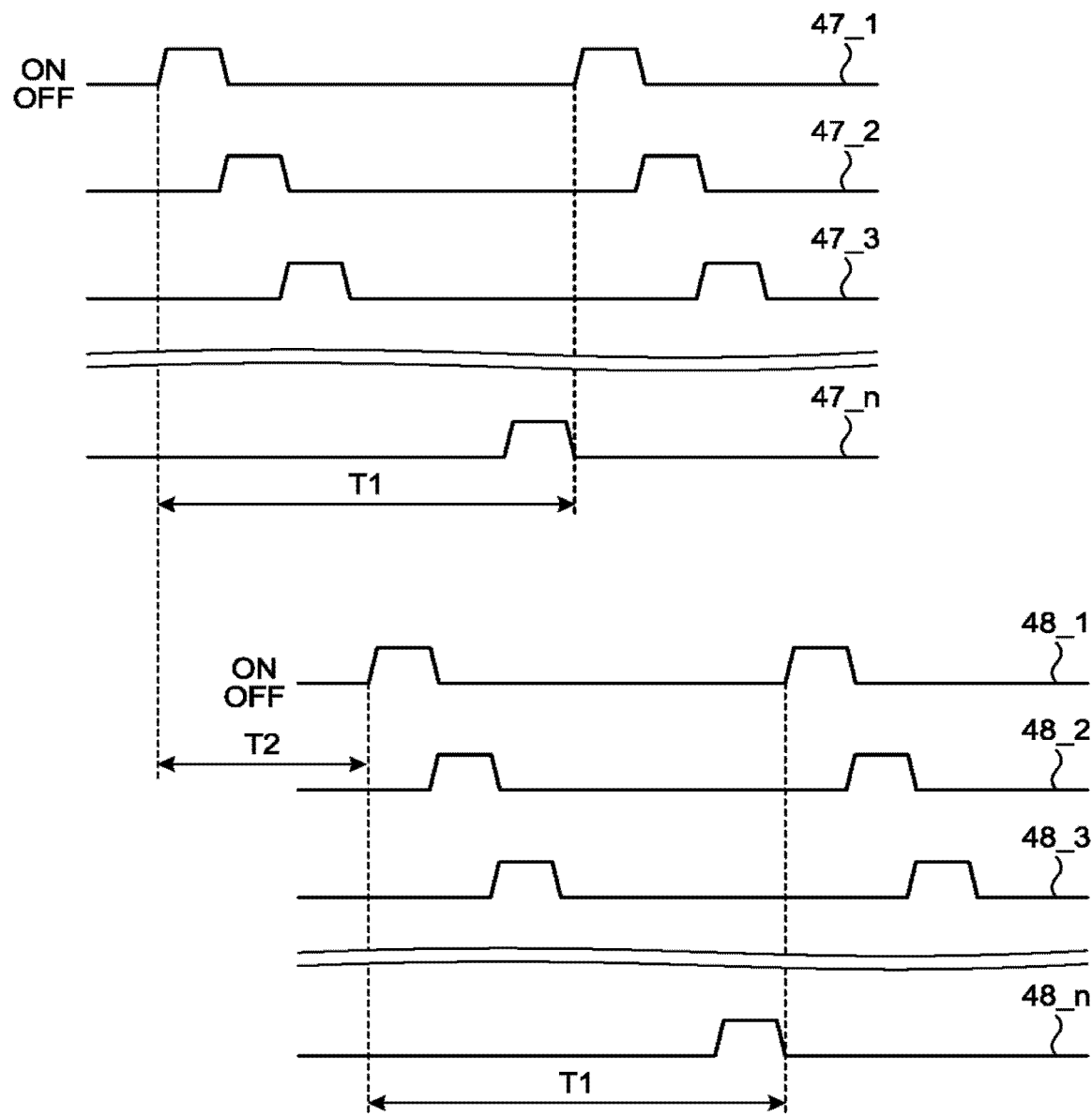
FIG. 4 is a chart illustrating examples of a plurality of write control signals and a plurality of read control signals according to the embodiment.

Next, examples of the write control signals and the read control signals according to the present embodiment will be explained, with reference to FIG. 4. FIG. 4 is a chart illustrating examples of a plurality of write control signals 47_1 to 47_n and a plurality of read control signals 48_1 to 18_n according to the embodiment.

The write control signal 47_k is input to the control signal input terminal 45_k. During the time periods when the write control signal 47_k indicates ON (a high level), the write switch 40_k allows electrical conduction between the echo signal input terminal 43 and the capacitor 41_k. In other words, the write switch 40_k arranges the echo signal input terminal 43 and the capacitor 41_k to be electrically connected to each other.

Further, during the time periods when the write control signal 47_k indicates OFF (a low level), the write switch 40_k blocks the electrical connection between the echo signal input terminal 43 and the capacitor 41_k.

As a result, during the time periods when the write control signal 47_k indicates ON, the capacitor 41_k stores an electrical charge therein. In other words, among the echo signals input to the echo signal input terminal 43, the capacitor 41_k samples the echo signals corresponding to the time periods when the write control signal 47_k indicates ON and stores therein the sampled echo signals.

Further, the capacitor 41_k does not store therein the echo signals corresponding to the time periods when the write control signal 47_k indicates OFF.

Among the plurality of write control signals 47_1 to 47_n, the state of indicating ON sequentially switches from one to another in a substantially continuous manner. For this reason, as schematically indicated by an arrow 52 (see FIG. 3), the analog delay circuitry 25 is configured so that the echo signals are sampled in certain periodic cycle and so that each of the echo signals corresponding to the sampling points in time is stored into a different one of the capacitors 41_1 to 41_n.

Further, each of the plurality of write control signals 47_1 to 47_n goes into the state of indicating ON in a predetermined periodic cycle T1. Further, after the write control signal 47_n goes into the state of indicating ON, the write control signal 47_1 again goes into the state of indicating ON. After that, among the plurality of write control signals 47_1 to 47_n, the state of indicating ON again sequentially switches from one to another in a substantially continuous manner.

Accordingly, as schematically indicated by an arrow 53 (see FIG. 3), the analog delay circuitry 25 is configured so that, after the sampled echo signal is stored into the capacitor 41_n, each of e echo signals that are subsequent to the echo signal (the sampled echo signal) stored in the capacitor 41_n and that correspond to a plurality of sampling points in time is stored so as to overwrite a corresponding one of the capacitors 41_1 to 41_n. Further, the storing operation described herein is repeatedly performed in the analog delay circuitry 25.

The read control signal 48_k is input to the control signal input terminal 46_k. During the time periods when the read control signal 49_k indicates ON, the read switch 42_k allows electrical conduction between the echo signal output terminal 44 and the capacitor 41_k. In other words, the read switch 42_k arranges the echo signal output terminal 44 and the capacitor 41_k to be electrically connected to each other.

Further, during the time periods when the read control signal 48_k indicates OFF, the read switch 42_k blocks the electrical connection between the echo signal output terminal 44 and the capacitor 41_k.

As a result, during the e periods when the read control signal 48_k indica ON, the capacitor 41_k releases the electrical charge. In other words, the read switch 42_k reads the echo signal sampled and stored in the capacitor 41_k and arranges the read echo signal to be output from the echo signal output terminal 44.

Further, during the time periods when the read control signal 41_k indicates OFF, the capacitor 41_k keeps storing therein the sampled echo signal.

As for the read control signal 46_k, the state of indicating ON is exhibited as being delayed, by a predetermined delay time period T2, from the state of the write control signal 47_k indicating ON. Accordingly, the echo signal sampled and stored in the capacitor 41_k is read when the predetermined delay time period T2 has elapsed since the echo signal is stored in the capacitor 41_k. The delay time period T2 is a value unique to the individual piece of analog delay circuitry 25.

Further, among the plurality of read control signals 48_1 to 48_n, the state of indicating ON sequentially switches from one to another in a substantially continuous manner. For this reason, as schematically indicated by an arrow 54 (see FIG. 3), the analog delay circuitry 25 is configured so that each of the plurality of sampled echo signals is read from a different one of the capacitors 41_1 to 41_n.

Further, similarly to the plurality of write control signals 47_1 to 47_n, each of the plurality of read control signals 48_1 to 48_n goes into the state of indicating ON in the predetermined periodic cycle T1. Further, after the read control signal 48_n goes into the state of indicating ON, the read control signal 48_1 again goes into the state of indicating ON. After that, among the plurality of read control signals 48_1 to 46_n, the state of indicating ON again sequentially switches from one to another in a substantially continuous manner.

Accordingly, the analog delay circuitry 25 is configured so that, after the sampled echo signal is read from the capacitor 41_n, each of the echo signals that are subsequent to the echo signal read from the capacitor 41_n and that correspond to a plurality of sampling points in time is read from a corresponding one of the capacitors 41_1 to 41_n. Further, the reading operation described herein is repeatedly performed in the analog delay circuitry 25.

In this situation, the periodic cycle T1 has a value corresponding to the quantity of the plurality of capacitors 41_1 to 41_n. The quantity of the plurality of capacitors 41_1 to 41_n is equal to a value corresponding to a maximum delay amount in the delay process performed by the analog delay circuitry 25. For this reason, it is safe to say that the periodic cycle T1 has a value corresponding to the maximum delay amount in the delay process performed by the analog delay circuitry 25.

As explained above, the write control signal 47_k and the read control signal 48_k each have periodicity where the stat of indicating ON is repeated in the periodic cycle T1. Due to the periodicity of the write control signal 47_k and the read control signal 48_k, a frequency component (a spurious component) that is unintended in the design is superimposed as a noise component on the echo signals and the addition signal. Such noise may be referred to as periodic noise, for example.

For example, a noise component is superimposed on the echo signals output from the phase reversal processing circuitry 24 connected to the analog delay circuitry 25 via the wiring 30. Further, a noise component is also superimposed on the addition signals output from the adding circuitry 26 and the output buffer 27 connected to the analog delay circuitry 25 via the wiring 30. Furthermore, a noise component is also superimposed on the echo signals output from the analog delay circuitry 25. These noise components are exhibited as ghost noise in ultrasound images.

Figure 5:
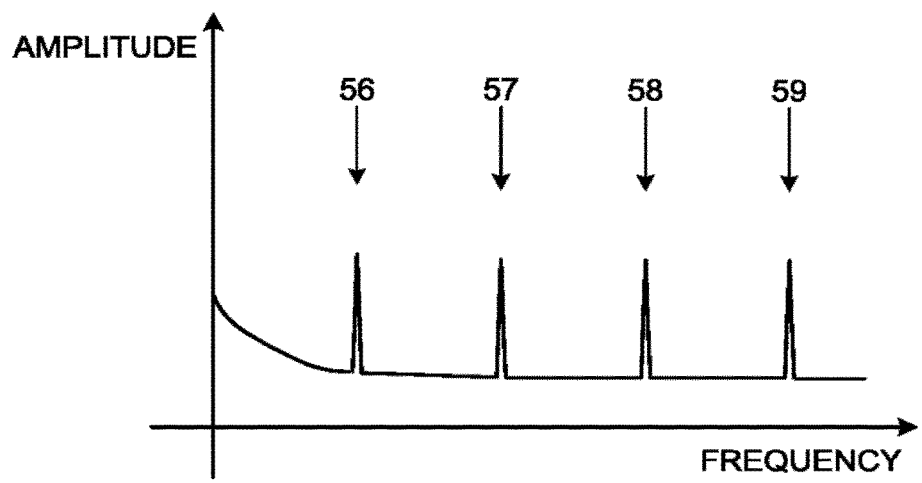
FIG. 5 is a chart for explaining examples of noise components superimposed on either an echo signal or an addition signal.

FIG. 5 is a chart for explaining examples of the noise components superimposed on either an echo signal or an addition signal. FIG. 5 illustrates a result of a frequency analysis performed on either the echo signal or the addition signal. The horizontal axis expresses frequency, whereas the vertical axis expresses amplitude.

As illustrated in FIG. 5, the component at a fundamental frequency (1/T1) indicated by an arrow 56 includes a noise component. Further, the components at the multiples ((2/T1), (3/T1), and (4/T1)) of the fundamental frequency indicated by arrows 57 to 59 each also includes a noise component.

Figure 6:
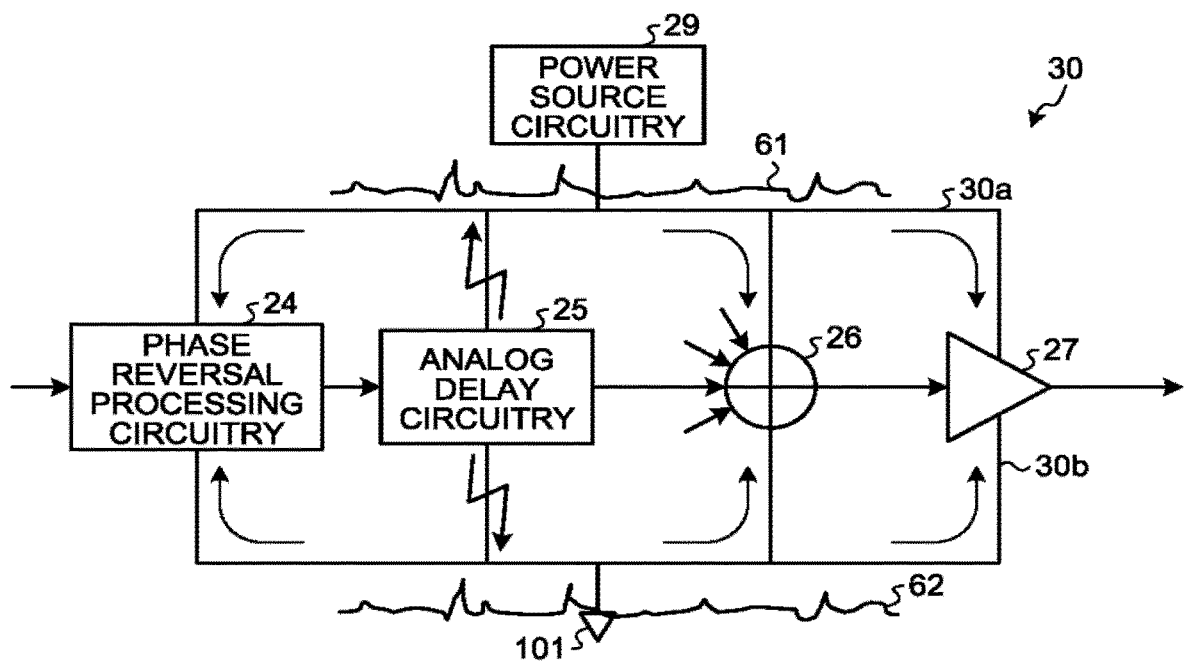
FIG. 6 is a diagram for explaining an example of a reason why noise components are superimposed on echo signals and addition signals.

Next, an example of a reason why the noise components are superimposed on the echo signals and the addition signals will be explained, with reference to FIG. 6. FIG. 6 is a diagram for explaining the example of the reason why the noise components are superimposed on the echo signals and the addition signals. FIG. 6 schematically illustrates a part of the elements structuring the ultrasound probe 1.

As illustrated in FIG. 6, the wiring 30 includes a wiring 30a and a wiring 30b. The wiring 30a is connected to the power source circuitry 29, the phase reversal processing circuitry 24, the analog delay circuitry 25, the adding circuitry 26, and the output buffer 27. The wiring 30b is connected to the phase reversal processing circuitry 24, the analog delay circuitry 25, the adding circuitry 26, the output buffer 27, and a ground 101.

FIG. 6 illustrates a waveform 61 that schematically indicates a relationship between time and the magnitude of the voltage (power source voltage) applied to the phase reversal processing circuitry 24, the analog delay circuitry 25, the adding circuitry 26, and the output buffer 27 by the power source circuitry 29. Further, FIG. 6 illustrates a waveform 62 that schematically indicates a relationship between time and the magnitude of the ground voltage. The waveform 61 and the waveform 62 may be obtained by an oscilloscope, for example.

It is desirable that the power source voltage and the ground voltage each be constant. However, due to the periodicity explained above, the analog delay circuitry 25 causes the value of the power source voltage to fluctuate, as indicated by the waveform 61. For the same reason, the analog delay circuitry 25 causes the value of the ground voltage to fluctuate, as indicated by the waveform 62. In other words, due to the periodicity, the analog delay circuitry 25 electrically causes the power source voltage and the ground voltage to fluctuate.

When the value of the voltage applied by the power source circuitry 29 fluctuates in this manner, noise components are periodically superimposed on the echo signals output from the phase reversal processing circuitry 24 and the analog delay circuitry 25. Further, noise components are periodically superimposed also on the echo signals output from the adding circuitry 26 and the output buffer 27.

In other words, as for sources from which the noise caused by the periodicity occur, it is considered that the analog delay circuitry 25 is a direct source that causes the noise, whereas the phase reversal processing circuitry 24, the adding circuitry 26, and the output buffer 27 are indirect sources that cause the noise.

Figure 7:
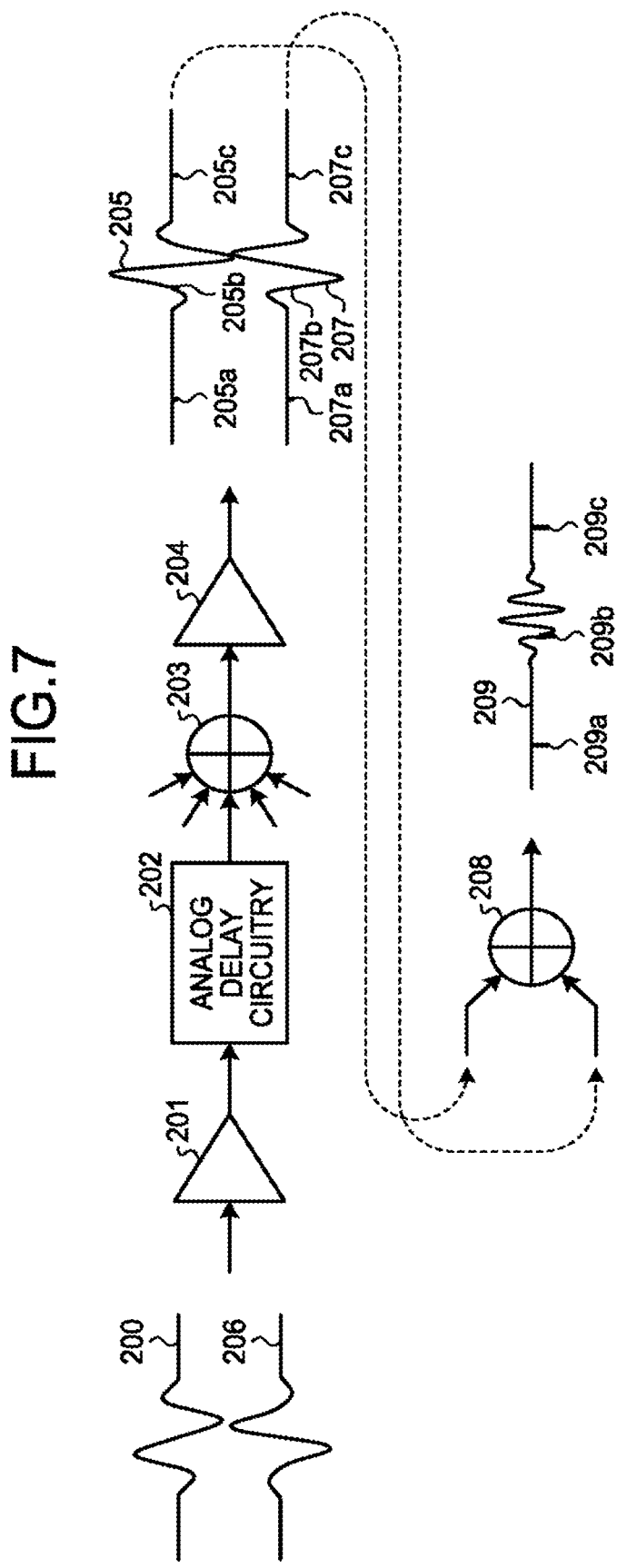
FIG. 7 is a diagram for explaining an example of a method called a pulse inversion method.

Incidentally, when a tissue harmonic imaging process is implemented by using a method called a pulse inversion (pulse subtraction) method, noise components are emphasized. According to the method called the pulse inversion method, an image signal in which a fundamental wave component is suppressed while a second harmonic wave component is emphasized is used for generating a picture. FIG. 7 is a diagram for explaining an example of the method called the pulse inversion method.

For example, according to the pulse inversion method, as illustrated in FIG. 7, a first echo signal 200 is amplified by a preamplifier 201. Further, the amplified first echo signal 200 is delayed by analog delay circuitry 202. After that, a plurality of delayed first echo signals 200 are added together by adding circuitry 203 to become one signal (a first addition signal) 205. Subsequently, the first addition signal 205 is output from an output buffer 204.

On a second echo signal 206 also, the same processes are performed by the preamplifier 201, the analog delay circuitry 202, and the adding circuitry 203, so that a second addition signal 207 is output from the output buffer 204.

On the first addition signal 205, noise components 205a, 205b, and 205c caused by the periodicity explained above are superimposed. Further, on the second addition signal 207, noise components 207a, 207b, and 207c caused by the periodicity explained above are superimposed. In this situation, the noise components 205a, 205b, and 205c have the same phases as the noise components 207a, 207b, and 207c, respectively.

After that, an image signal 209 is generated by adding circuitry (the adder) 208 by adding together the first addition signal 205 and the second addition signal 207. In this situation, because the noise component 205a and the noise component 207a have the same phase as each other, a noise component 209a resulting from adding together the noise component 205a and the noise component 207a is superimposed on the image signal 209. For the same reason, a noise component 209b resulting from adding together the noise component 205b and the noise component 207b as well as another noise component 209c resulting from adding together the noise component 205c and the noise component 207c are superimposed on the image signal 209. The noise components 209a, 209b, and 209c are each an emphasized noise component.

As a result, in the harmonic imaging process using the method called the pulse inversion method, the noise components caused by the periodicity are emphasized.

Figure 8:
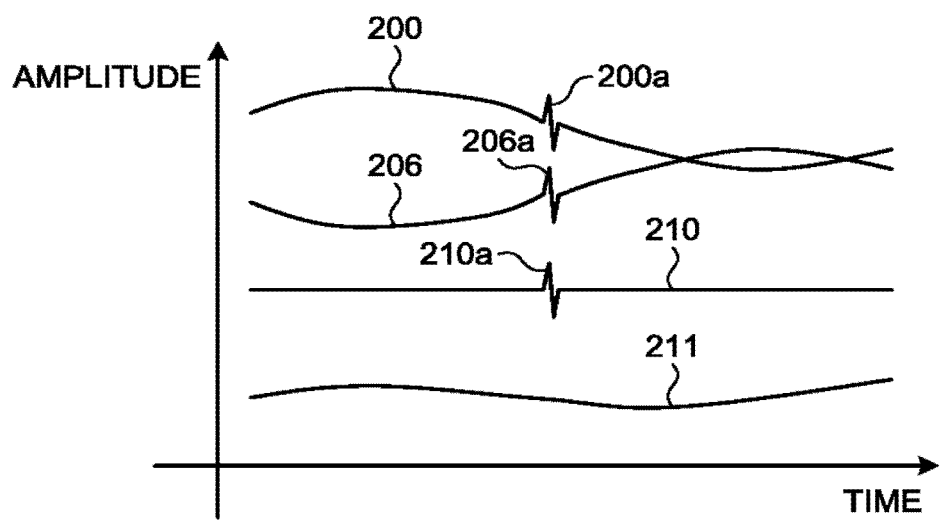

Further, it is also possible to perform a process explained below, for the purpose of reducing the noise components caused by the periodicity. FIG. 8 is a drawing for explaining an example of the process performed for the purpose of reducing the noise components caused by the periodicity.

FIG. 8 illustrates the first echo signal 200, the second echo signal 206, a canceling signal 210, and an image signal 211. In FIG. 8, the horizontal axis expresses time, whereas the vertical axis expresses amplitude.

The canceling signal 210 is an echo signal output by a transducer element of an ultrasound probe without transmitting an ultrasound wave. In other words, the canceling signal 10 is an echo signal that is output without receiving an echo of an ultrasound wave.

Further, the ultrasound probe calculates the image signal 211 used for generating a picture, by using Expression (1) presented below.

$$VS = TR1 + TR2 - 2*\text{Noise} \quad (1)$$

In Expression (1), "TR1" denotes the first echo signal 200, whereas "TR2" denotes the second echo signal 206. Further, "Noise" denotes the canceling signal 210, while "VS" denotes the image signal 211. In Expression (1), "*" serves as a multiplication symbol.

As illustrated in FIG. 8, noise 200a superimposed on the first echo signal 200 and the noise 206a superimposed on the second echo signal 206 are suppressed in the image signal 211 by noise 210a superimposed on the canceling signal 210. In this manner, in the image signal 211 the noise components caused by the periodicity explained above are reduced.

However, to generate one image signal, in addition to the process of adding together the first echo signal 200 and the second echo signal 206, it is necessary to perform the process of subtracting the canceling signal 210 from the result of the addition. In other words, to obtain echo data corresponding to on scan line, it is necessary to perform the adding/subtracting process twice. Accordingly, there is a possibility that the frame rate may be lowered.

In this situation, as indicated in Expression (1), the adding/subtracting process is performed on the three signals (echo signals), namely "TR1", "TR2", and "Noise". For example, when the quantity of the signals on which the adding/subtracting process is performed is expressed as "s", the amount of noise of a random nature other than the noise caused by the periodicity is proportional to "$s^{1/2}$". Accordingly, when the noise caused by the periodicity is suppressed by using Expression (1), the amount of noise of a random nature, which is calculated as "$(3/2)^{1/2}$" times larger than that when "TR1" and "TR2" are added together, increases.

To cope with this situation, the ultrasound diagnosis apparatus 100 according to the present embodiment is configured to be able to suppress the noise included in the echo signals and the addition signal while preventing the frame rate from being lowered.

FIG. 9 is a diagram illustrating an exemplary configuration of the phase reversal processing circuitry 24 according to the embodiment. As illustrated in FIG. 9, the phase reversal processing circuitry 24 includes switches 71 and 72, phase-reversal and amplification circuitry 73, differential/single-end conversion circuitry 74.

The switch 71 includes terminals 75 to 77. The terminal 75 is earthed to a ground. The terminal 76 is connected to the corresponding transmission/reception switch 22. The terminal 77 is connected to the phase-reversal and amplification circuitry 73. More specifically, the terminal 77 is connected, via a resistor 82 (explained later), to a normal-phase input terminal 81a of a fully differential amplifier 81 (explained later).

Under control of the digital controlling circuitry 28, the switch 71 is configured to switch between: first conduction state in which electrical conduction is allowed between the terminal 76 and the terminal 77; and a second conduction state in which electrical conduction is allowed between the terminal 75 and the terminal 77.

In the first conduction state, an echo signal from the transmission/reception switch 22 is input to the phase-reversal and amplification circuitry 73. In contrast, in the second conduction state, the normal-phase input terminal 81a of the fully differential amplifier 81 (explained later) is earthed to the ground via the resistor 82 (explained later). Further, in the second conduction state, an echo signal from the transmission/reception switch 22 is not input to the phase-reversal and amplification circuitry 73 via the switch 71.

The switch 72 includes terminals 78 to 80. The terminal 78 is earthed to a ground. The terminal 79 is connected to the corresponding transmission/reception switch 22. The terminal 80 is connected to the phase-reversal and amplification circuitry 73. More specifically, the terminal 80 is connected, via a resistor 84 (explained later) to a reversed-phase input terminal 81b of the fully differential amplifier 81 (explained later).

Under control of the digital controlling circuitry 28, the switch 72 is configured to switch between: a third conduction state in which electric conduction is allowed between the terminal 79 and the terminal 80; and a fourth conduction state in which electric conduction is allowed between the terminal 78 and the terminal 80.

In the third conduction state, an echo signal from the transmission/reception switch 22 is input to the phase-reversal and amplification circuitry 73. In contrast, in the fourth conduction state, the reversed-phase input terminal 81b of the fully differential amplifier 81 (explained later) is earthed to the ground via the resistor 84 (explained later). Further, in the fourth conduction state, an echo signal from the transmission/reception switch 22 is not input to the phase-reversal and amplification circuitry 73 via the switch 72.

The phase-reversal and amplification circuitry 73 includes the fully differential amplifier 81 and the resistors 82 to 85. The fully differential amplifier 81 includes the normal-phase (non-reversal) input terminal 81a, the reversed-phase (reversal) input terminal 81b, a reversed-phase output terminal 81c, and a normal-phase output terminal 81d.

One end of the resistor 82 is connected to the terminal 77. The other end of the resistor 82 is connected to the normal-phase input terminal 81a. One end of the resistor 83 is connected to the normal-phase input terminal 61a. The other end of the resistor 83 is connected to the reversed-phase output terminal 81c.

One end of the resistor 84 is connected to the terminal 80. The other end of the resistor 84 is connected to the reversed-phase input terminal 81b. One end of the resistor 85 is connected to the reversed-phase input terminal 81b. The other end of the resistor 85 is connected to the normal-phase output terminal 81d.

The differential/single-end conversion circuitry 74 is configured to convert a differential signal into a single-end signal. The differential/single-end conversion circuitry 74 includes an operational amplifier 86 and resistors 87 to 90.

The operational amplifier 86 includes a reversed-phase input terminal 86a, a normal-phase input terminal 86b, and an output terminal 86c. One end of the resistor 87 is connected to the reversed-phase output terminal 81c. The other end of the resistor 87 is connected to the reversed-phase input terminal 86a. One end of the resistor 88 is connected to the reversed-phase input terminal 86a. The other end of the resistor 88 is connected to the output terminal 86c.

One end of the resistor 89 is connected to the normal-phase output terminal 81d. The other end of the resistor 89 is connected to the normal-phase input terminal 86b. One end of the resistor 90 is connected to the normal-phase input terminal 86b. The other end of the resistor 90 is earthed to a ground.

In this situation, an example will be explained in which the ultrasound diagnosis apparatus 100 according to the present embodiment performs a tissue harmonic imaging process. For instance, an example in which the first echo signal is input to the chase reversal processing circuitry 24 will be explained. In that situation, as illustrated in FIG. 9, the switch 71 sets the conduction state to the first conduction state, whereas the switch 72 sets the conduction state to the fourth conduction state. In other words, the first echo signal is input to the normal-phase input terminal 81a of the fully differential amplifier 81, while the potential of the reversed-phase input terminal 81b is equal to the ground potential. In this manner, a differential signal is input to the fully differential amplifier 81.

Next, a relationship among $v_{in}$, $v_{out}$, $v_{d+}$, $v_{d-}$, $R_1$, $R_2$, $R_3$, and $R_4$ corresponding to the situation where the switch 71 sets the conduction state to the first conduction state, whereas the switch 72 sets the conduction state to the fourth conduction state will be explained.

In this situation, $v_{in}$ denotes the potential (the input voltage) of the terminals 76 and 79; $v_{out}$ denotes the potential (the output voltage) of the output terminal 860; $v_{d+}$ denotes the potential (the output voltage) of the normal-phase output terminal 81d; and $v_{d-}$ denotes the potential (output voltage) of the reversed-phase output terminal 81c. Further, $R_1$ denotes the resistance value of the resistor 82 and the resistor 84. $R_2$ denotes the resistance value of the resistor 83 and the resistor 85. $R_3$ denotes the resistance value of the resistor 87 and the resistor 89. $R_4$ denotes the resistance value of the resistor 88 and the resistor 90.

It is possible to express $v_{out}$ by using Expression (2) presented below.

$$V_{out} = \frac{R_4}{R_3} \cdot (V_{d+} - V_{d-}) \qquad (2)$$

Further, it is possible to express the difference between $v_{d+}$ and $v_{d-}$ ($v_{d+}-v_{d-}$) by using Expression (3) presented below.

$$(V_{d+} - V_{d-}) = \frac{R_2}{R_1} \cdot V_{in} \qquad (3)$$

From Expressions (2) and (3), it is possible to express $v_{out}$ by using Expression (4) presented below.

$$V_{out} = \frac{R_4}{R_3} \cdot \frac{R_2}{R_1} \cdot V_{in} \qquad (4)$$

In the present embodiment, the resistors 82 to 85 and 87 to 90 that make "$R_4/R_3 \cdot R_2/R_1$" in Expression (4) larger than 1 are used. For this reason, it is possible to arrange $v_{out}$ to be larger than $v_{in}$. In other words, the phase reversal processing circuitry 24 is configured to amplify the first echo signal.

Further, in Expression (4), the phases (the polarities) of $v_{in}$ and $v_{out}$ are the same as each other. In this manner, the phase reversal processing circuitry 24 transmits the amplified first echo signal, without reversing the phase thereof.

Next, an example will be explained in which the second echo signal is input to the phase reversal processing circuitry 24. FIG. 10 is a chart for explaining the example in which the second echo signal is input to the phase reversal processing circuitry 24.

As illustrated in FIG. 10, the switch 71 sets the conduction state to the second conduction state, whereas the switch 72 sets the conduction state to the third conduction state. In other words, the second echo signal is input to the reversed-phase input terminal 81b of the fully differential amplifier 81, whereas the potential of the normal-phase input terminal 81a is equal to the ground potential. In this manner, a differential signal is input to the fully differential amplifier 81.

A relationship among $v_{in}$, $v_{out}$, $v_{d+}$, $v_{d-}$, $R_1$, $R_2$, $R_3$, and $R_4$ in this situation will be explained. It is possible to express $v_{out}$ by using Expression (5) presented below.

$$V_{out} = \frac{R_4}{R_3} \cdot (V_{d+} - V_{d-}) \qquad (5)$$

Further, it is possible to express the difference between $v_{d+}$ and $v_{d-}$ ($v_{d+}-v_{d-}$) by using Expression (6) presented below.

$$(V_{d+} - V_{d-}) = -\frac{R_2}{R_1} \cdot V_{in} \qquad (6)$$

From Expression (5) and (6), it is possible to express out by using Expression (7) presented below.

$$V_{out} = -\frac{R_4}{R_3} \cdot \frac{R_2}{R_1} \cdot V_{in} \qquad (7)$$

In Expression (7), the phases of $v_{in}$ and $v_{out}$ are opposite to each other. When the phase of $v_{in}$ is reversed and amplified, the result is $v_{out}$. In this manner, the phase reversal processing circuitry 24 reverses the phase of the second echo signal and amplifies the phase-reversed second echo signal.

As explained above, the phase reversal processing circuitry 24 has a phase reversing function to reverse the phase of the second echo signal and an amplifying function to amplify the first echo signal and the second echo signal.

As additional information, when a normal ultrasound scan is performed, the switch 71 sets the conduction state to the first conduction state, whereas the switch 72 sets the conduction state to the fourth conduction state.

Next, an exemplary configuration of the B-mode processing circuitry 12 will be explained, with reference to FIG. 11. FIG. 11 is a diagram illustrating the exemplary configuration of the B-mode processing circuitry 12.

As illustrated in FIG. 11, the B-mode processing circuitry 12 includes subtracting circuitry (a subtractor) 12a, logarithmic amplification circuitry 12b, and envelope detection processing circuitry 12c. In the following sections, an example in which a harmonic imaging process performed will be explained.

The first echo data described below is echo data obtained as a result of the transmission and reception circuitry 11 converting the first addition signal in an analog format into the first addition signal in a digital format and further performing a phased addition process on first addition signals in the digital format. Further, the second echo data described below is echo data obtained as a result of the transmission and reception circuitry 11 converting the second addition signal in an analog format into the second addition signal in a digital format and further performing a phased addition process on second addition signals in the digital format. In other words, the first echo data is data corresponding to the first addition signal, whereas the second echo data is data corresponding to the second addition signal.

The subtracting circuitry 12a is configured, when the first echo data is transmitted thereto from the transmission and reception circuitry 11, to store the first echo data into a memory of the subtracting circuitry 12a (or the storage circuitry 15). Further, the subtracting circuitry 12a is configured, when second echo data is transmitted thereto from the transmission and reception circuitry 11, to read the first echo data from the memory (or the storage circuitry 15).

In this situation, the first echo data and the second echo data have the same phase as each other. Accordingly, to obtain an image signal in which the second harmonic wave component is emphasized, the subtracting circuitry 12a generates (creates) the image signal by performing a subtracting process while using the first echo data and the second echo data. For example, the subtracting circuitry 12a performs a subtracting process of subtracting the second echo data from the first echo data. In this manner, the subtracting circuitry 12a generates the echo data obtained as a result of subtracting the second echo data from the first echo data, as the image signal.

The logarithmic amplification circuitry 12b is configured to perform a logarithmic amplification process on the image signal. The envelope detection processing circuitry 12c is configured to generate B-mode data by performing an envelope detection process on the image signal on which the logarithmic amplification process was performed.

When a normal ultrasound scan is performed, in the B-mode processing circuitry 12, a logarithmic amplification process is performed by the logarithmic amplification circuitry 12b on input echo data, and an envelope detection process is performed by the envelope detection processing circuitry 12c on the echo data on which the logarithmic amplification process was performed.

Next, an example of a flow in processes will be explained, with reference to FIG. 12. FIG. 12 is a diagram for explaining an example of a flow in various types of processes performed by the ultrasound diagnosis apparatus 100 according to the embodiment.

For example, the phase reversal processing circuitry 24 reverses the phase of a second echo signal 93, as being selected from between a first echo signal 92 and the second echo signal 93. In this manner, the phase reversal processing circuitry 24 reverses the phase of the second echo signal 93, before the noise caused by the periodicity is superimposed on the first echo signal 92 and the second echo signal 93. The first echo signal 92 and the phase-reversed second echo signal 93 have the same phase as each other.

Further, the analog delay circuitry 25 delays the first echo signal 92. After that, the adding circuitry 26 generates a first addition signal 95 by adding together a plurality of delayed first echo signals. The adding circuitry 26 outputs the generated first addition signal 95 to the apparatus main body 10 via the output buffer 27.

Further, the analog delay circuitry 25 delays the second echo signal 93. After that, the adding circuitry 26 generates a second addition signal 96 by adding together plurality of delayed second echo signals. The adding circuitry 26 outputs the generated second addition signal to the apparatus main body 10 via the output buffer 27.

In this situation, on the first addition signal 95, noise components 95a, 95b, and 95c caused by the periodicity are superimposed. Further, on the second addition signal 96 also, noise components 96a, 96b, and 96c caused by the periodicity are superimposed. The noise components 95a, 95b, and 95c have the same phases as the noise components 96a, 96b, and 96c, respectively.

Further, the subtracting circuitry 12a generates an image signal 97 by performing a subtracting process while using the first echo data corresponding to the first addition signal 95 and the second echo data corresponding to the second addition signal 96. For example, in a subtraction to subtract the second echo data from the first echo data, the noise component 96a is subtracted from the noise component 95a. Similarly, the noise component 96b is subtracted from the noise component 95b, whereas the noise component 96c is subtracted from the noise component 95c. As a result, the ultrasound diagnosis apparatus 100 according to the present embodiment is able to obtain the image signal 97 in which the second harmonic wave component is emphasized, while the fundamental wave component is suppressed, and also, the noise components caused by the periodicity are suppressed.

Further, to generate one ultrasound image, because the subtracting circuitry 12a storms the subtracting process to subtract the second echo a from the first echo data, the adding/subtracting process needs to be performed only once. For this reason, the ultrasound diagnosis apparatus 100 according to the present embodiment performs the adding/subtracting process a smaller number of times compared to the example illustrated in FIG. 8. It is therefore possible to prevent the frame rate from being lowered.

Consequently, the ultrasound diagnosis apparatus 100 according to the present embodiment is able to suppress the noise superimposed on the echo signals and the addition signal, while preventing the frame rate from being lowered.

Further, in the ultrasound diagnosis apparatus 100 according to the present embodiment, the quantity of pieces of echo data used for the subtracting process performed by the subtracting circuitry 12a is two (i.e., the first echo data and the second echo data). Accordingly, the amount of noise of a random nature, which is calculated as "$(2/3)^{1/2}$" times larger than that in the example illustrated in FIG. 8, is reduced.

Further, although the example is explained in which the apparatus main body 10 includes the subtracting circuitry 12a, another arrangement is also acceptable in which the ultrasound probe 1 includes subtracting circuitry having the same functions as those of the subtracting circuitry 12a.

Further, although the example is explained in which the single piece of phase reversal processing circuitry 24 has the phase reversing function and the amplifying function explained above, another arrangement is also acceptable in which circuitry having the phase reversing function and circuitry having the amplifying function are separately provided.

By using the ultrasound probe and the ultrasound diagnosis apparatus according to at least one aspect of the embodiments described above, it is possible to suppress the noise superimposed on the echo signals and the addition signal, while preventing the frame rate from being lowered.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound probe comprising:
   a plurality of transducer elements configured to:
      generate a plurality of first echo signals respectively by receiving, at a first time at each respective transducer element of the plurality of transducer elements, a reflected wave of a first ultrasound wave, and
      generate a plurality of second echo signals respectively by receiving, at a second time at each respective transducer element of the plurality of transducer elements, a reflected wave of a second ultrasound wave corresponding to an ultrasound wave obtained by reversing a phase of the first ultrasound wave, wherein the second time is different than the first time;
   phase reversal processing circuitry configured to reverse phases of only the plurality second echo signals; and
   delay processing circuitry configured to delay the plurality of first echo signals and the plurality of phase-reversed second echo signals.

2. The ultrasound probe according to claim 1, wherein the phase reversal processing circuitry comprises a plurality of phase reversal processing circuits and the delay processing circuitry comprises a plurality of delay processing circuits, and
   wherein the plurality of transducer elements are configured to output said plurality of first echo signals to the plurality of phase reversal processing circuits respectively, and the plurality of phase reversal circuits are configured to output said plurality of first echo signals to the plurality of delay processing circuits respectively, and
   wherein the plurality of transducer elements are configured to output said plurality of second echo signals to the plurality of phase reversal processing circuit s respectively, and the plurality of phase reversal processing circuits are configured to output said plurality of phase-reversed second echo signals to the plurality of delay processing circuits respectively.

3. The ultrasound probe according to claim 1, wherein the phase reversal processing circuitry is configured to amplify the plurality of first echo signals and the plurality of phase-reversed second echo signals, and the delay processing circuitry is configured to delay the amplified plurality of first echo signals and the amplified plurality of phase-reversed second echo signals.

4. The ultrasound probe according to claim 1, further comprising:
adding circuitry configured to generate a first addition signal by adding together two or more delayed first echo signals, of the delayed plurality of first echo signals, corresponding to two or more transducer elements of the plurality of transducer elements and to generate a second addition signal by adding together two or more phase-reversed and delayed second echo signals, of the delayed plurality of phase-reversed second echo signals, corresponding to said two or more transducer elements.

5. The ultrasound probe according to claim 4, further comprising:
subtracting circuitry configured to generate an image signal by performing a subtracting process on the first addition signal and the second addition signal.

6. The ultrasound probe according to claim 1, further comprising:
power source circuitry and
a wiring connecting together the power source circuitry, the phase reversal processing circuitry, and the delay processing circuitry,
wherein the power source circuitry is configured to apply a voltage to the phase reversal processing circuitry and to the delay processing circuitry, via the wiring, thereby operating the phase reversal processing circuitry and the delay processing circuitry, and
wherein the delay processing circuitry is analog circuitry.

7. The ultrasound probe according to claim 4, further comprising:
power source circuitry and
a wiring connecting together the power source circuitry, the phase reversal processing circuitry, the delay processing circuitry, and the adding circuitry,
wherein the power source circuitry is configured to apply a voltage to the phase reversal processing circuitry, to the delay processing circuitry, and to the adding circuitry, via the wiring, thereby operating the phase reversal processing circuitry, the delay processing circuitry, and the adding circuitry and
wherein the delay processing circuitry is analog circuitry.

8. The ultrasound probe according to claim 1, further comprising:
controlling circuitry configured to transmit, to the delay processing circuitry, a digital control signal having a waveform which periodically changes and which controls the delay of the plurality of first echo signal and the plurality of phase-reversed second echo signals realized by the delay processing circuitry.

9. An ultrasound diagnosis apparatus comprising:
an ultrasound probe including:
a plurality of transducer elements configured to:
generate a plurality of first echo signals respectively by receiving, at a first time at each respective transducer element of the plurality of transducer elements, a reflected wave of a first ultrasound wave and,
generate a plurality of second echo signals respectively by receiving, at a second time at each respective transducer element of the plurality of transducer elements, a reflected wave of a second ultrasound wave corresponding to an ultrasound wave obtained by reversing a phase of the first ultrasound wave, wherein the second time is different than the first time;
phase reversal processing circuitry configured to reverse phases of only the plurality of second echo signals,
delay processing circuitry configured to delay the plurality of first echo signals and the plurality of phase-reversed second echo signals, and
adding circuitry configured to:
generate a first addition signal by adding together two or more delayed first echo signals, of the delayed plurality of first echo signals, corresponding to two or more transducer elements of the plurality of transducer elements, and
generate a second addition signal by adding together two or more phase-reversed and delayed second echo signals, of the delayed plurality of phase-reversed second echo signals, corresponding to said two or more transducer elements; and
subtracting circuitry configured to generate an image signal by performing a subtracting process using the first addition signal and the second addition signal.

* * * * *